United States Patent [19]

Hutchins et al.

[11] 4,026,292
[45] May 31, 1977

[54] TAMPON HAVING A MENSESPHILIC FOAM TREATED WITH A LIQUID LUBRICANT

[75] Inventors: James P. Hutchins, Cincinnati; Robert D. Dobson, Greenhills, both of Ohio

[73] Assignee: The Procter & Gamble Company, Cincinnati, Ohio

[22] Filed: Sept. 17, 1974

[21] Appl. No.: 506,828

[52] U.S. Cl. ............................ 128/285; 128/270; 428/307; 428/314; 428/327; 428/403; 428/405; 428/407

[51] Int. Cl.² ........................................ A61F 13/20

[58] Field of Search ............... 260/2.5 AD; 252/12, 252/14; 161/168; 210/36, 40; 128/270, 285; 428/407, 405, 543, 497, 327, 314, 307, 447, 403

[56] References Cited

UNITED STATES PATENTS

| | | | |
|---|---|---|---|
| 3,249,465 | 3/1966 | Chen | 260/2.5 AD |
| 3,306,966 | 2/1967 | Matejcek | 128/285 |
| 3,344,212 | 9/1967 | Francis | 428/403 |
| 3,548,892 | 12/1970 | Olson | 128/270 |
| 3,591,524 | 7/1971 | Eriksen | 210/40 |
| 3,608,593 | 9/1971 | McCormick | 128/270 |
| 3,676,357 | 7/1972 | Ciuti | 210/36 |
| 3,681,237 | 8/1972 | Orban | 210/36 |
| 3,794,029 | 2/1974 | Dulle | 128/270 |
| 3,808,129 | 4/1974 | Lindlof | 252/12 |
| 3,815,601 | 6/1974 | Schaefer | 128/270 |

FOREIGN PATENTS OR APPLICATIONS 251,076  11/1962  Australia

*Primary Examiner*—Ellis Robinson
*Attorney, Agent, or Firm*—John M. Pollaro; Frederick H. Braun; John V. Gorman

[57] ABSTRACT

Improving the handling characteristics of flexible, resilient, particulate polyurethane foam by adding a small quantity of liquid lubricant to the surface of the foam to prevent clumping. Applying as little as about 0.5 percent to about 20 percent by weight of a liquid lubricant such as mineral oil to the surface of the particulate foam facilitates more uniform filling of equal-volume containers with particles of said foam and reduces the container-to-container weight variation.

4 Claims, 1 Drawing Figure

TAMPON HAVING A MENSESPHILIC FOAM TREATED WITH A LIQUID LUBRICANT

FIELD OF THE INVENTION

The present invention relates generally to disposable absorbent structures suitable for the collection and retention of body exudates, particularly to sanitary napkins and tampons, and even more particularly to preferred methods for constructing such structures with a more uniform quantity of absorbent material in each unit.

DESCRIPTION OF THE PRIOR ART

A wide variety of absorbent materials have been employed in prior art catamenial structures for the purpose of absorbing and retaining body exudates. More prior art tampons which can be inserted by the user are generally rigid structures constructed primarily of cellulosic fibrous materials which exhibit a high modulus of compression, a very low resiliency, and are small in cross-section in order to attain insertion, wearing, and removal comfort.

In more recently developed absorbent structures, polyurethane foam has been utilized as an absorbent body to overcome many of the aforementioned drawbacks associated with prior art fibrous cores. For example, U.S. Pat. No. 3,749,029 which issued to Dulle on Feb. 26, 1974 and which is hereby incorporated herein by reference discloses an improved, open-celled, flexible, resilient, "mensesphilic" polyurethane foam tampon structure having a transverse periphery large enough to substantially coincide with the periphery of the vagina, and a shaped modulus of compression which allows it to be deformed by the vertical pressure exerted by the vagina, whereby the tampon spreads laterally to more completely establish contact with the walls of the vagina and prevent bypass of menses. As used herein, a "mensesphilic" material shall be broadly defined as one with which menstrual fluid makes a contact angle of less than 90°. In general, this contact angle is adequate to define a material which performs well in absorbing menses in normal tampon wearing times ranging from about one to about eight hours.

U.S. Pat. No. 3,815,601 which issued to Schaefer on June 11, 1974 and which is hereby incorporated herein by reference discloses still another improved absorbent tampon structure wherein the absorbent body is preferably comprised of an aggregate of separate pieces of flexible, resilient, mensesphilic polyurethane foam of the type described in the aforementioned patent to Dulle. The aggregate is held together by an encasing overwrap which is relatively loose about the aggregate to permit some relative motion between adjacent particles of foam. The mesh of the overwrap is fine enough to totally contain the absorbent particles from and thereby prevent surfaces of the absorbent particles from penetrating the overwrap and forming part of the external surface of the tampon. The absorbent tampon structure disclosed in the patent to Schaefer establishes a large void volume, i.e., unoccupied space within the absorbent body and the vagina which will act as reservoir for menstrual fluid, very soon after insertion into the body cavity and thereafter maintains the void volume. Therefore, the tampon disclosed in the patent to Schaefer has greater absorbent capacity than prior art tampons, it is large enough to fill out substantially the entire cross-section of the vagina upon insertion, and consequently provides containment of discharged menses. In addition, it has a large available surface area which promotes a favorable absorption rate, and it is comfortable to insert, wear, and remove.

The absorbent body of the tampon structure described in the patent to Schaefer is preferably comprised of an aggregate of various sized pieces or of substantially uniformly sized pieces of mensesphilic polyurethane foam. The particle sizes can range from about $\frac{1}{16}$ inch to about 1 inch, but are preferably from about $\frac{1}{16}$ inch to about $\frac{3}{8}$ inch. Prior to loading the particles of foam into the tampon overwrap, the foam is preferably washed in water and dried to remove any extraneous materials. However, the particulate foam, especially after washing and drying, tends to clump together. This is undesirable in that it makes consistently filling a uniform amount of chopped foam into each absorbent tampon structure extremely difficult. Since the absorption characteristics of the finished tampon are dependent to a great extent on the amount of absorbent foam contained in the structure, large variations in foam weight which occur from one tampon to the next are extremely undesirable.

Typical of prior art techniques for improving the handling characteristics of difficulty handled materials is U.S. Pat. No. 3,548,892 issued to Olson on Dec. 22, 1970 which teaches the increasing of the bulk density of low-density cellular strands of material in bulk storage and improved handling and dispensing of the strands by maintaining them in a liquid, preferably water, which is both inert to and non-solvent for the strands. U.S. Pat. No. 3,608,593 issued to McCormick, Jr. et al. on Sept. 28, 1971 likewise teaches the filling of bottles, ampoules, vials and the like with difficulty handled powders by suspending the powder in an inert, volatile, liquid diluent, filling the suspension into the desired container and evaporating the inert, liquid diluent leaving only the dry powder in the container.

Applicants, on the other hand, have discovered that the handling characteristics of particulate polyurethane foam such as that employed in preferred embodiments of the absorbent tampon structure described in the aforementioned patent to Schaefer can be greatly improved without adversely affecting the absorbency characteristics of the foam by adding a relatively small quantity of a low viscosity, liquid lubricant to the surface of the foam after the washing and drying operations. Addition of the liquid lubricant to the surface of the particulate foam reduces the clumpiness of the foam, thereby improving its flowability. This in turn facilitates more uniform filling of equal-volume containers with particles of the foam and reduces the container-to-container weight variation.

Applicants have further learned that both hydrophobic liquid lubricants such as mineral oil and hydrophilic liquid lubricants such as glycerine are effective in improving the handling characteristics of particulate foam as described herein.

Due to the hydrophilic nature of lubricants such as glycerine, however, there is a tendency of absorbent structures treated with such materials to attract moisture from the atmosphere during storage prior to use. Depending upon such factors as humidity, length of time in storage, concentration of the lubricant in the absorbent structure, etc., an absorbent structure treated with a hydrophilic lubricant may undergo premature expansion due to moisture pick-up prior to use, thereby making insertion of the absorbent structure into the body cavity more difficult, and, in the case of an absorbent tampon structure inserted by means of a disposable inserting mechanism of the type generally disclosed in the aforementioned patent to Schaefer, may considerably increase the force required to eject the absorbent tampon structure into the vagina from the disposable inserter mechanism. Therefore, in a most preferred embodiment of applicant's invention, hydrophobic lubricants which have no inherent tendency to attract moisture from the surrounding atmosphere are preferred.

OBJECTS OF THE INVENTION

Accordingly, it is an object of the present invention to provide a method for improving the handling characteristics of flexible, resilient, particulate polyurethane foams by adding a small quantity of low viscosity, liquid lubricant to the surface of the foam to promote flowability and prevent clumping, thereby permitting more consistent weight control in high speed filling operations without adversely affecting the absorbency characteristics of the foams.

SUMMARY OF THE INVENTION

In a preferred embodiment of the present invention there is provided a method of improving the handling characteristics of particulate polyurethane foam by adding a small quantity of low viscosity, liquid lubricant to the surface of the foam to prevent clumping. Application of the liquid lubricant to the surface of the particulate foam, particularly after washing and drying of the foam, facilitates more uniform filling of equal-volume containers with particles of said foam. Addition of the liquid lubricant to the surface of the particulate foam typically permits more dense packing of the foam particles into the equal-volume filling containers while reducing the container-to-container weight variation, thereby providing more consistent weight control in the finished tampon structure.

In yet another preferred embodiment of the present invention a lubricant-treated polyurethane foam structure which exhibits minimal dimensional changes when stored under varying atmospheric conditions is provided.

In still another preferred embodiment of the present invention a lubricant-treated foam which exhibits a less severe compression "set" or permanent compression deformation when stored for extended periods under compression is provided. Thus the foam's favorable expansion characteristics upon insertion into a body cavity are preserved.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in connection with the accompanying drawings, in which:

DETAILED DESCRIPTION OF THE PREFERRED EMBODIMENTS

Figure 1:
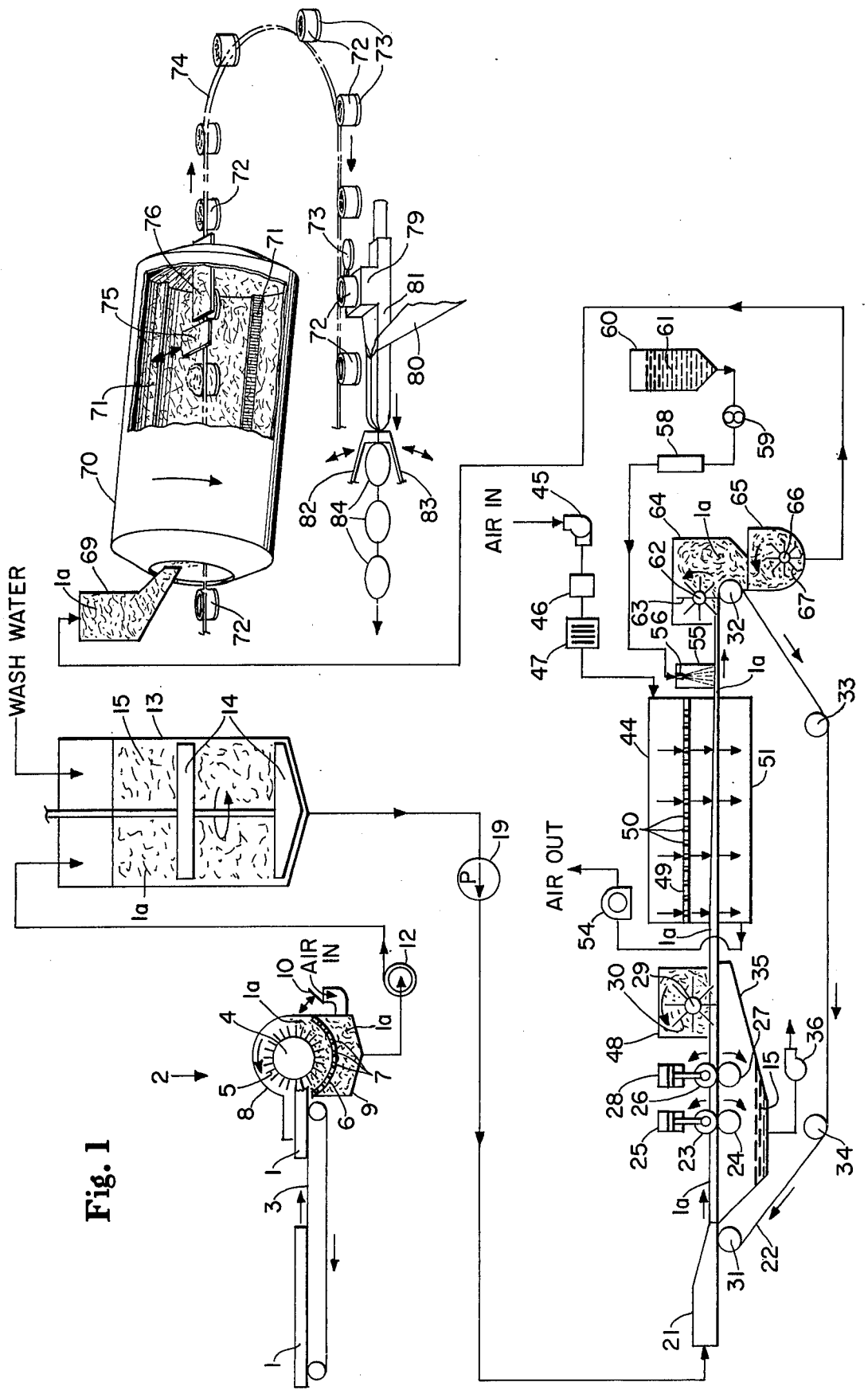
FIG. 1 is a simplified schematic diagram of a preferred process for shredding slabs of polyurethane foam into particulate form and for treating the particulate foam with a liquid lubricant to improve its handling characteristics prior to filling a plurality of equal-volume metering containers used to supply individual quantities of foam to a tampon forming operation.

FIG. 1 is a simplified schematic diagram of a preferred process for converting slabs of polyurethane foam of the type suitable for use in disposable absorbent structures from slab form to a free-flowing, particulate form exhibiting favorable handling characteristics. The process described herein has been found particularly suitable on mensesphilic polyurethane foams of the type described in U.S. Pat. No. 3,815,601 which issued to Schaefer on June 11, 1974 and U.S. Pat. No. 3,794,029 which issued to Dulle on Feb. 26, 1974, said patents being incorporated herein by reference. Since the mensesphilic polyurethane foam utilized in the structure of Schaefer is in particulate form, however, the process described herein has particular relevance with respect to the fabrication process for structures of that general type.

As shown in FIG. 1, slabs of polyurethane foam 1 having a thickness of approximately 6 inches, a width of approximately 10 inches, and a length between about 6 and 8 feet are fed into a suitable chopping apparatus 2 for reduction to particulate form. The chopping apparatus 2 is preferably comprised of an infeed conveyor 3 which advances the slabs of polyurethane foam 1 into a closed chamber 8 housing a rotating cylinder 4 having a plurality of cutting blades 5 projecting from its periphery. As the slabs of polyurethane foam 1 are advanced into the rotating cutting blades 5, the foam is reduced from a slab into particulate form 1a, said particulate foam accumulating generally toward the rear of the housing 8. A curved dividing plate 6 having a plurality of holes 7 therein separates the uppermost portion of the housing 8 from the lowermost portion of the housing 9. The lowermost portion of the housing 9 is maintained under negative pressure by means of a centrifugal blower 12 and an adjustable damper 10 mounted in the lowermost portion of the housing 9. Particles of chopped foam 1a which are sufficiently small to be drawn through the holes 7 in the dividing plate 6 are caused to enter the lowermost portion of the housing 9 due to the influence of the negative pressure maintained therein. Once in the lowermost portion of the housing 9, the particulate foam 1a is mixed with incoming air drawn primarily through the adjustable damper 10 and pneumatically conveyed by means of a centrifugal blower 12 to a wash tank 13 as illustrated in FIG. 1.

A commercially available chopping apparatus 2 such as the Fitz Mill Guilocutter, Model 20, Code No. 28LX18D, as manufactured by The Fitzpatrick Company of Elmhurst, Illinois, has been found particularly suitable for use in the process described herein.

The desired particle size distribution of the chopped foam 1a upon introduction to the wash tank 13 is preferably as follows:

- on ⅜ inch U.S. Sieve, from about 1 to about 5 percent of the particulate foam 1a will be retained;
- through ⅜ inch U.S. Sieve, on No. 6 U.S. Sieve, from about 79 to about 65 percent of the particulate foam 1a will be retained;
- through No. 6 U.S. Sieve, on No. 12 U.S. Sieve, from about 15 to about 20 percent of the particulate foam 1a will be retained; and
- through No. 12 U.S. Sieve, about 5 to about 10 percent of the particulate foam 1a will pass through.

Following the chopping operation, the particulate foam 1a is preferably subjected to a washing operation to remove water extractables from the foam and to ensure complete reaction of the components utilized in making the foam slabs 1. The process water 15 utilized during the washing operation is preferably dechlorinated to prevent the chlorine from yellowing the foam. In a preferred embodiment of the present invention, the process water 15 is further pretreated by means of a reverse osmosis system to reduce the dissolved solids content of the water to below about 50 parts per million. The foam washing operation is carried out with the contents of the wash tank 13 under constant agitation which is provided by means of a rotary agitator 14 at a water to foam ratio of at least about 40 to 1. The wash water temperature is preferably maintained between about 95° and about 105° F through the wash cycle to simulate extraction temperatures which are encountered by a finished tampon structure upon insertion into the human body. The length of the wash cycle is preferably between about 5 minutes and about 24 hours, and most preferably between about 1 hour and about 4 hours. If the particulate foam 1a is washed for too short a period of time, the levels of residual extractables will not be minimized, while if washed for too long a period of time, the risk of bacterial growth in the wash water is increased.

Upon completion of the wash cycle, a slurry comprised of the particulate foam 1a and the wash water 15 is fed from the wash tank 13 by means of a positive displacement pump 19 to a weir box distributor 21 where the particulate foam is distributed into a bed having an approximately uniform depth, and is subsequently dewatered, hot-air dried, and treated with liquid lubricant. The slurry is preferably introduced from the weir box distributor 21, which is of conventional papermaking design, onto the surface of an open-mesh dryer belt 22. One material which has been found particularly suitable for use as a dryer belt is a 36 × 30 mesh square-weave polyester fabric formed from monofilaments having a diameter of about 0.40 millimeters. In general, open-mesh polyester fabrics of the type utilized to imprint a knuckle pattern on a thermally pre-dried paper web as described in U.S. Pat. No. 3,301,746 which issued to Sanford et al. on Jan. 31, 1967 and which is hereby incorporated herein by reference have been found suitable.

The rate at which particulate foam 1a is deposited upon the dryer belt 22 is preferably controlled by regulating the speed of the positive displacement delivery pump 19. A foam thickness of between about 2 and about 3 inches prior to compression has been found desirable for use in conjunction with the present system. Due to the open-mesh construction of the dryer belt 22, the wash water portion 15 of the slurry passes through the dryer belt and is collected in a collection trough 35 underlying that portion of the dryer belt 22 located ahead of the hot air dryer hood 44. The wash water 15 collected in the drainage trough 35 may, by means of pump 36, be recycled to the wash tank 13 to aid in transferring the particulate foam 1a from the wash tank to the weir box 21 or may be disposed of directly.

The dryer belt 22 which rotates about fixed rolls 31, 32, 33 and 34 advances the particulate foam 1a deposited thereon between a pair of hard-surfaced compression rolls 23 and 24 to mechanically dewater the foam prior to entering the dryer hood 44. The nip pressure between the rolls 23 and 24 which extend across the entire width of the foam bed is preferably controlled by means of a pair of pneumatically or hydraulically controlled cylinders 25 which are regulated so as to cause the uppermost roll 23 to exert a constant pressure against the lowermost roll 24 underlying the dryer belt 22 and the foam bed. For an initial foam bed thickness between about 2 and about 3 inches, a nip roll pressure between about 20 and about 30 pounds per lineal inch has been found most desirable. A second set of compression rolls 26 and 27, identical in construction and operation to compression rolls 23 and 24, is preferably located downstream of compression rolls 23 and 24. Compression rolls 26 and 27 are likewise controlled by means of a pair of hydraulically or pneumatically actuated cylinders 28 which control the position of the uppermost roll 26 and consequently the nip pressure between rolls 26 and 27.

The mechanical dewatering provided by the two sets of hard-surfaces compression rolls preferably provides a foam bed containing approximately 2 pounds of wash water 15 per pound of air dry particulate foam 1a (i.e., as measured at a moisture content of about 5 percent) at the inlet to the hot air dryer hood 44.

A fluffer roll 29 having a plurality of mechanical fingers 30 mounted on its periphery is preferably mounted downstream of compression rolls 26 and 27 in an enclosed housing 48 to fluff up the bed of particulate foam 1a on the dryer belt 22 prior to hot air drying. Mechanically fluffing the foam prior to hot air drying reduces the formation of hydrogen bonds between foam particles during drying and thereby prevents the foam particles from bonding together. In addition, it promotes more efficient drying of the particulate foam 1a by increasing the porosity of the foam bed.

Air is drawn from the atmosphere by means of a centrifugal supply fan 45 and, subsequent to filtration to remove any undesirable particulate matter in air filter 46, is brought to a temperature between about 275° and about 350° F by means of a heat exchanger 47 prior to introduction into the uppermost section 44 of the hot air dryer hood. From the uppermost section of the dryer hood 44, the hot air is forced through a plurality of holes 50 in a baffle plate 49 located overhead of the dryer belt 22. The hot air is directed through the bed of particulate foam 1a and passes through the open-mesh dryer belt 22 into the lowermost section of the dryer hood 51 from whence it is collected and either recirculated to the suction side of the centrifugal supply fan or exhausted to the atmosphere as shown in FIG. 1 by means of a centrifugal exhaust fan 54. The air flow through the hot air dryer hood 44 and the speed of the dryer belt conveyor 22 are so regulated by means well known to those skilled in the art that the moisture content of the particulate foam 1a upon exit from the dryer hood 44 is about 5 percent. As illustrated in FIG. 1, reducing the moisture content of the foam bed as described herein normally causes a decrease in the thickness of the foam bed. Thus a foam bed containing about 2 pounds of wash water per pound of air dry foam and having a thickness of about 2 to about 3 inches at the entrance to the hot air dryer hood 44 typically has a thickness between about 1 and about 1½ inches upon exit from the hot air dryer hood.

Upon exit from the hot air dryer hood 44, the bed of particulate foam 1a passes within an enclosed spray chamber 55 where a regulated amount of liquid lubricant 61 is applied to its uppermost surface. The liquid lubricant 61 is transferred from a suitable storage tank 60 by means of a positive displacement metering pump 59 to an atomizing nozzle 56 which is centrally located at the uppermost surface of the spray chamber 55. For any given mass flow rate of foam as determined by the speed of the dryer belt 22, the amount of liquid lubricant 61 applied to the uppermost surface of the bed of particulate foam 1a is controlled by varying the drive speed of the positive displacement metering pump 59 by means well known in the art. A flow meter 58 is preferably installed in the delivery line between the metering pump 59 and the spray nozzle 56 to monitor the flow rate of the liquid lubricant 61. For a bed of air dry mensesphilic polyurethane foam 1a having a thickness of between about 1 and about 1½ inches, a width of about 23 inches, and an air dry density of about 2 pounds per cubic foot, applicants have found that a single, centrally-located atomizing spray nozzle 56 having a single 0.75 inch long by 0.040 inch wide slit therein mounted approximately 12 inches above the uppermost surface of the foam with the length dimension of the slit perpendicularly oriented to the direction of travel of the dryer belt 22 will produce a lubricant application level of about 1 percent, based on the use of mineral oil applied at a flow rate of approximately 20 cubic centimeters per minute through the spray nozzle 56, at a dryer belt speed of approximately 9 feet per minute. Since the mass flow rate of the foam 1a passing within the spray chamber 55 can readily be determined for any given speed of the dryer belt 22 by means well known in the art, the lubricant application level can be adjusted to the desired target either by varying the speed of the metering pump 59 to obtain the desired flow rate through the flow meter 58 or by varying the speed of the dryer belt 22. Applicants have found a Zenith Lab Metering Pump Model No. BPB-4391-297, as manufactured by Zenith Products Company of West Newton, Massachusetts, to be particularly suitable for use as a metering pump 59 with the foam lubrication system described herein, while a Pneumatic Standard Nozzle, Series No. ¼ J, Model No. 14, as manufactured by the Spraying System Company of Bellwood, Illinois, has been found satisfactory as an atomizing spray nozzle 56. As should be apparent to those skilled in the art, the selection of the particular components utilized in the foam lubrication system is largely a matter of choice, the chief criterion being the ability of the system to produce an atomized spray throughout the desired range of lubricant flow rates.

In order to produce a significant improvement in the handling characteristics of the particulate polyurethane foam 1a, the amount of lubricant 61 added is preferably between about 0.5 percent and about 20 percent, based upon the air dry weight of the particulate foam (i.e., containing about 5 percent moisture), and most preferably between about 1 percent and about 5 percent. At concentrations less than about 0.5 percent, the handling characteristics, i.e., the clumpiness of the particulate foam 1a, are not significantly improved, while at concentrations above about 20 percent, the foam develops an objectionably oily feel, and leaves an oily residue on the hands when touched. This is not only generally viewed as a product negative by consumers when the foam is employed in an absorbent structure such as a tampon, but also makes packaging of the finished absorbent structure more difficult since packaging materials ordinarily employed for this purpose are easily soiled by the excess lubricant.

Since only the uppermost surface of the particulate foam bed 1a is subjected to the lubricant spray in the closed chamber 55 in the system described herein, the foam is thereafter subjected to a mixing operation to distribute the lubricant 61 applied to its uppermost surface more uniformly throughout the particulate foam. This is preferably accomplished by feeding the particulate foam 1a into a closed chamber 64 housing a fluffer roll 62 having a plurality of mechanical fingers 63 secured to its periphery. The rotating fluffer roll 62 dislodges the foam from the surface of the dryer belt 22 in addition to rupturing any bonds which may have been formed between the various particles of foam during the pressing and drying operations. After removal from the dryer belt 22, the particulate foam 1a is introduced into a mechanical blender such as a Marion Mixer Model No. 1254, as manufactured by the Rapids Machinery Company of Marion, Iowa. The blender 65 houses a rotating cylinder 66 having a plurality of impeller blades 67 secured to its periphery throughout its length. The particulate foam 1a is introduced at one end of the blender and, due to the action of the impeller blades 67, is caused to move to the opposite end of the blender where it is discharged after the mechanical mixing operation has been completed. The degree of agitation provided by means of the mechanical blender 65 should be sufficient to obtain approximately uniform distribution of the lubricant applied to the uppermost surface of the foam bed. Applicants have typically obtained satisfactory lubricant distribution throughout the desired range of lubricant concentrations with a blender cylinder speed of about 130 revolutions per minute at a foam mass flow rate through the blender of about 4 pounds of foam per minute.

After the mixing operation, the treated particulate foam 1a may be placed in suitable containers and stored until ready for final use or transmitted directly to a tampon manufacturing operation such as that described in the copending and commonly assigned application of Schaefer, Ser. No. 484,813, filed July 1, 1974 for Apparatus and Method for Continuously Forming and Filling Tampon Sacks, said application being hereby incorporated herein by reference. In the latter instance, the particulate foam 1a is deposited in a supply hopper 69 which is utilized to introduce the particulate foam to a rotating drum 70 having a plurality of blades 71 projecting inwardly from its innermost periphery. The elevation of the drum 80 is slightly greater at its infeed end so that the particulate foam 1a is caused to distribute itself along the length of the drum. Thus, as the drum rotates, the particulate foam is continuously lifted by the plurality of longitudinal blades 71 secured to its innermost surface. The rotation of the drum 70 thereby creates a "rain" of foam particles throughout the interior of the drum. As illustrated in FIG. 1, a plurality of equal-volume filling containers 72 is secured to a continuous chain 74 which is guided through the interior of the rotating drum 70. Each container 72 secured to the chain 74 is equipped with a pivotally-mounted bottom plate 73. The contents of each container 72 is utilized to fill a tubular tampon structure formed with a suitable overwrap material 80 on the tube forming mandrel 81. The volume of each container 72 with its lowermost plate 73 in the closed position is equal to that of each of the other containers 72 secured to the chain 74. The containers 72 are guided through the interior of the rotating drum 70 with their lowermost plates 73 in the closed position and are filled by the "rain" of particulate foam prevailing along the interior sections of the drum. As the chain 74 is indexed through the interior of the rotating drum 70 the particulate foam fills each container 72 to the point of overflowing. To equalize the amount of foam contained in each container 72, the uppermost surface of each container is brought into contact with a reciprocating knife 75 located near the discharge end of the rotating drum 70. The reciprocating knife 75 removes the excess particulate foam from each container prior to the container's passing beneath a protective baffle plate 76 which prevents the deposition of additional particulate foam into the containers after the aforementioned trimming operation. The filled containers 72 are thereafter indexed into position over the tampon filling hopper 79, whereupon the lowermost plate 73 of the container 72 is cammed open and the particulate foam 1a contained therein is introduced through the hopper 79 and tube forming mandrel 81 into successive tubular segments of overwrap material 80, the ends of which are thereafter sealed by means of sealing jaws 82 and 83 to form an interconnected chain of filled tampon sacks 84 as described in greater detail in the aforementioned copending application of Schaefer.

As should be apparent to those skilled in the art, the particular volumetric filling apparatus utilized is largely a matter of choice, depending upon the particular circumstances. For example, the following references describe filling apparatus of the type generally described herein, said references being hereby incorporated herein by reference: U.S. Pat. No. 2,719,661 issued to Eisenberg on Oct. 4, 1955; U.S. Pat. No. 2,937,670 issued to Eisenberg on May 24, 1960; U.S. Pat. No. 2,978,231 issued to Eisenberg on Apr. 4, 1961; U.S. Pat. No. 3,217,760 issued to Eisenberg on Nov. 16, 1955; and U.S. Pat. No. 3,298,404 issued to Eisenberg on Jan. 17, 1967.

Applicants have learned that treatment of the particulate foam 1a with a low viscosity, liquid lubricant as described herein greatly reduces the clumpiness inherent in the foam, particularly after washing and drying, thereby permitting a considerable improvement in weight control in a volumetric filling operation of the type generally described herein. This factor is important to the quality of the finished product in that more uniform filling of the tampon sacks will provide more consistent product performance. An additional benefit provided by the lubricant treatment described herein is a reduction in the severity of the compression "set" or permanent compression deformation assumed by the foam when stored for extended periods under compression, thus preserving the foam's favorable expansion characteristics upon insertion into a body cavity. This is of particular importance where the tampon structure may be stored in a disposable inserter mechanism for a considerable length of time prior to use. It is applicant's belief that the lubricant treatment preserves the foam's expansion characteristics by minimzing particle-to-particle hydrogen bonding as well as minimizing wall-to-wall or strut-to-strut hydrogen bonding within individual foam particles.

To illustrate the dramatic effect of lubricant treatment on fill weight variations, several samples of mensesphilic polyurethane foam were selected from a commonly produced lot of foam, and all but the first such sample were treated generally in accordance with the process described herein, but a different concentration of liquid lubricant was applied to each sample. The particular lubricant employed was AMOCO 18 USP mineral oil, as supplied by the American Oil Company of Whiting, Indiana. Each sample of foam was then processed through a volumetric filling apparatus of the type described generally herein. The filling apparatus employed equal-volume filling containers, each having a volume of approximately 12.5 cubic inches. A total of 50 containers were filled with each foam sample, and the average container fill weight and standard deviation were calculated from the data collected. The results are set forth in the table below.

| Example No. | Concentration of lubricant in foam based on the air dry weight of the foam (percent) | Average Weight of foam in each container (grams) | Standard Deviation in weight between containers of foam (grams) |
|---|---|---|---|
| I | 0 | 2.32 | 0.30 |
| II | 0.5 | 1.96 | 0.18 |
| III | 2.0 | 1.95 | 0.12 |
| IV | 4.0 | 2.15 | 0.08 |

As should be apparent from the data set forth in Examples I through IV above, addition of a relatively small quantity of mineral oil to the foam reduces the container-to-container weight variation.

Applicants have learned that while lubricant concentrations as low as about 0.5 percent are beneficial, increasing the lubricant concentration beyond about 5 percent does not provide corresponding improvements in the tampon filling operation described herein. In addition, applicants have learned that lubricant concentrations beyond about 20 percent may introduce other serious product negatives such as excessive oily feel not only of the foam itself but also of the finished tampon structure. In addition, lubricant concentrations beyond about 20 percent may create an unsanitary appearance in the finished product packaging materials due to soiling by the excess lubricant.

Therefore, in a preferred embodiment of the present invention, applicants prefer to utilize lubricant concentrations between about 0.5 percent and about 20 percent, and most preferably between about 1 percent and about 5 percent, based upon the air dry weight of the particulate foam.

A number of liquid lubricants have been found suitable for improving the handling characteristics of particulate polyurethane foams of the type generally described herein. Generally non-volatile materials known to act as a lubricant and having a viscosity at a temperature of approximately 100° F of between about 10 and about 1,000 centipoise, most preferably between about 100 and about 400 centipoise, are suitable. As used herein, a non-volatile lubricant shall be defined as one which is not readily vaporizable at room temperature. Since a preferred use of the treated polyurethane foam is typically in an absorbent tampon structure, however, it is preferable that the lubricant employed be non-toxic and non-irritant to the human body, and further that the material not adversely affect the absorbency characteristics of the tampon structure.

Materials which have been found generally satisfactory by applicants in improving the foam's handling characteristics include, for example, mineral oil, glycerine, monoglycerides, vegetable oil, silicone oil, and fiber lubricants known generally in the industry. Of the aforementioned materials, mineral oil is most preferred due to its known safety in connection with the human body and its hydrophobic nature. Glycerine, on the other hand, although satisfactory from a safety standpoint, is hydrophilic in nature. It therefore tends to pick-up moisture from the atmosphere during extended period of storage under high humidity conditions. This is undesirable, particularly in an absorbent tampon structure, since moisture pick-up in the finished tampon can produce dimensional change due to growth, thereby resulting in increased difficulty of insertion as well as increased ejection forces from the tampon inserter. Therefore, hydrophobic lubricants which have no inherent tendency to attract moisture from the atmosphere are generally preferred where the ultimate use of the treated foam is in an absorbent structure such as a tampon.

As alluded to earlier herein, the particular lubricant selected for use in the present system should preferably have no adverse effect on the absorbency characteristics of the mensesphilic polyurethane foam, particularly where the ultimate use of the foam is an absorbent structure such as a tampon. Applicants have determined that even at lubricant concentration levels as high as about 20 percent, based on the air dry weight of the foam, neither hydrophobic lubricants such as mineral oil nor hydrophilic lubricants such as glycerine produce any significant adverse effect on either the total absorbent capacity or the rate of absorption of the foam.

Many modifications of the invention described herein can be made and it is not intended to limit the invention to the particular structures and methods described, all reasonable equivalents thereof being intended to fall within the scope of the invention.

What is claimed is:

1. A tampon having an absorbent means wherein said absorbent means is a free-flowing particulate mensesphilic polyurethane foam containing between about 0.5 percent and about 5 percent by weight of a non-volatile, hydrophobic liquid lubricant, based on the air dry weight of said foam, said lubricant having a viscosity of between about 100 and about 400 centipoise as measured at a temperature of about 100° F, said particulate foam expanding upon being placed in a body cavity and before being wetted, said particulate foam exhibiting no significant dimensional changes due to moisture pick-up from the atmosphere after extended period of storage under high humidity conditions.

2. A tampon having an absorbent means wherein said absorbent means is a free-flowing particulate mensesphilic polyurethane foam containing mineral oil, said mineral oil comprising, by weight, between about 0.5 percent and about 5 percent based on the air dry weight of said foam, said mineral oil having a viscosity of between about 100 and about 400 centipoise as measured at a temperature of about 100° F, said particulate foam expanding upon being placed in a body cavity and before being wetted, said particulate foam exhibiting no significant dimensional changes due to moisture pick-up from the atmosphere after extended periods of storage under high humidity conditions.

3. A tampon having an absorbent means wherein said absorbent means is a free-flowing particulate mensesphilic foam containing between about 0.5 percent and 20 percent by weight of a non-volatile, liquid lubricant, based on the air dry weight of said foam, said lubricant having a viscosity between about 10 and about 1,000 centipoise as measured at a temperature of about 100° F, said particulate foam expanding upon being placed in a body cavity and before being wetted exhibiting no significant dimensional changes due to moisture pick-up from the atmosphere after extended periods of storage under high humidity conditions.

4. A tampon having an absorbent means wherein said absorbent means is a free-flowing particulate mensesphilic foam containing between about 0.5 percent and 5 percent mineral oil, by weight, based on the air dry weight of said mensesphilic foam, said mineral oil having a viscosity of between about 100 and about 400 centipoise as measured at a temperature of about 100° F, said particulate foam expanding upon being placed in a body cavity and before being wetted, said particulate foam exhibiting no significant dimensional changes due to moisture pick-up from the atmosphere after extended periods of storage under high humidity conditions.

* * * * *